United States Patent
Tanriverdi

[11] Patent Number: 5,269,331
[45] Date of Patent: Dec. 14, 1993

[54] AUTOMATIC LOCKING AND ADJUSTABLE TENSION CONTROLLED DENTAL FLOSSER

[76] Inventor: Verdi F. Tanriverdi, 13171 Ethelbee Way, Santa Ana, Calif. 92705

[21] Appl. No.: 803,081

[22] Filed: Dec. 4, 1991

[51] Int. Cl.⁵ .......................................... A61C 15/00
[52] U.S. Cl. .................................................. 132/325
[58] Field of Search .............. 132/323, 324, 325, 326, 132/327

[56] References Cited

U.S. PATENT DOCUMENTS

| | | | |
|---|---|---|---|
| 2,047,456 | 7/1936 | Barsch | 132/325 |
| 3,734,107 | 5/1973 | Thierman | 132/325 |
| 3,746,017 | 7/1973 | Casselman | 132/325 |
| 3,759,272 | 9/1973 | DiVincenti | 132/326 |
| 3,908,677 | 9/1975 | Beach | 132/325 |
| 4,008,728 | 2/1977 | Sanchez | 132/324 |
| 4,178,947 | 12/1979 | McCourry et al. | 132/324 |
| 4,396,326 | 6/1980 | Eckroat | 132/326 |
| 4,508,125 | 4/1985 | Loubier | 132/326 |
| 4,518,000 | 5/1985 | Leverette | 132/325 |
| 4,574,823 | 3/1986 | Uriss | 132/325 |
| 4,655,234 | 4/1987 | Bowden | 132/325 |
| 4,738,271 | 4/1988 | Bianco | 132/323 |
| 4,827,952 | 5/1989 | Kos | 132/323 |
| 4,898,196 | 2/1990 | Eason | 132/326 |
| 4,901,742 | 2/1990 | Olson | 132/325 |
| 4,920,993 | 5/1990 | Mackie | 132/324 |
| 5,038,806 | 8/1991 | Ewald | 132/325 |

Primary Examiner—John J. Wilson
Attorney, Agent, or Firm—Stetina & Brunda

[57] ABSTRACT

A self-contained dental flosser, with adjustable tension control and auto-tension locking mechanism, allows flosser to operate and advance the floss continuously in one direction by rotating the spool where the spool gears extend out of the main frame. Operation is as simple as rotating the spool by thumb and adjusting the tension by one finger, if necessary. The flosser contains a total of three parts: 1) an elongated body with a lid containing two stabilizing cylinders, a locking mechanism, two prongs set on an angle for effortless flossing, hollow axles in separate compartments, and a separation wall, 2) one spool for holding the clean floss and 3) the second spool for holding the used floss.

8 Claims, 2 Drawing Sheets

U.S. Patent  Dec. 14, 1993  Sheet 2 of 2  5,269,331 ly, no dental flosser has been designed to# AUTOMATIC LOCKING AND ADJUSTABLE TENSION CONTROLLED DENTAL FLOSSER

FIELD OF INVENTION

This invention facilitates oral hygiene providing for a hand held flosser, which both holds fresh floss and retains used floss for disposal.

BACKGROUND OF THE INVENTION

Today, no one doubts the importance of oral hygiene and the use of floss to remove debris that can cause tartar and gum disease where a regular toothbrush cannot reach. The problem with flossing is that use of a loose strand of floss is unsanitary, clumsy, wasteful, and time-consuming. Floss comes in contact with fingers and the surrounding environment and it is no longer sanitary at the point of contact with mouth and gums. Keeping proper tension while flossing is also troublesome. To date, no dental flosser has been designed to remedy these problem areas.

SUMMARY OF THE INVENTION

This invention solves the problems mentioned above. This tool was invented to provide a sanitary, functional, ergonomic, and economic flossing device. Once the spools and floss are in place, the lid is closed and the stabilizing cylinders, with the locking mechanism, meet the gears on top of the spools keeping the tension at an optimum level. If additional tension is desired, the user simply presses the spot on the lid directly above the clean floss spool while, at the same time, dialing the used floss spool whose gears extend outside of the main frame. When the user desires more clean floss, he simply dials the used floss spool in the same manner. This self-contained, self-adjustable invention will automatically control and lock the tension, therefore making daily flossing effortless. The angled prongs will reach any part of the gums and teeth easily. The device is held and operated in only one hand, with the thumb dialing the extending spool, and one finger applying pressure if additional tension is needed. The floss advances within the self-contained body and the prongs keep the floss away from possible contact to the environment, rendering it very sanitary. Prongs also lock the floss at the tip so as to prohibit it from accidentally pulling out. However, it can also be removed easily by releasing the tension. It eliminates floss waste. Clean floss can be advanced even while it is in use and the floss is in contact with the teeth and gums. This device can only rotate in one direction when the lid is closed. The invention will be produced from a suitable plastic.

DETAILED DESCRIPTION OF THE INVENTION

Figure 1:
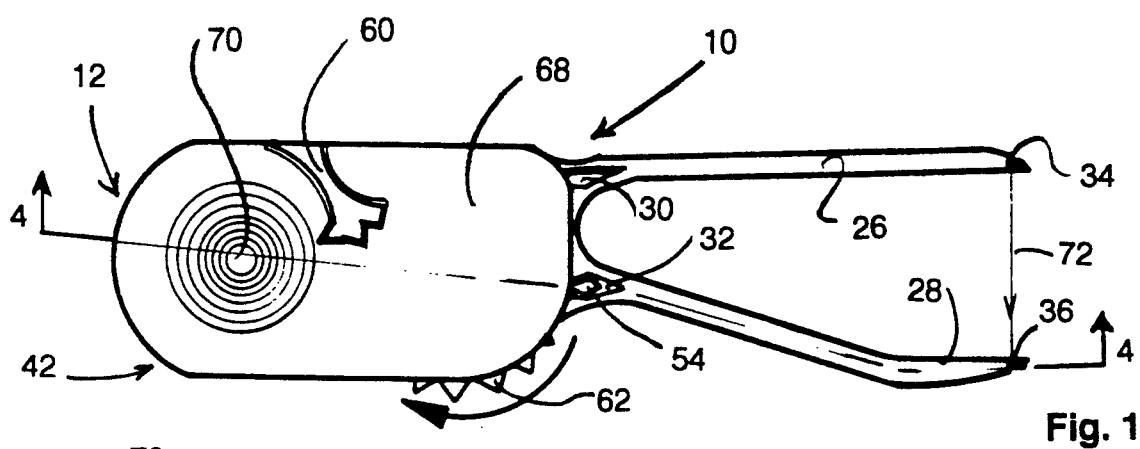
FIG. 1 is a top view of the invention.

Referring now to the drawings wherein the showings are for purposes of illustrating a preferred embodiment of the present invention only, and not for purposes of limiting the same, FIGS. 1-8 illustrate a dental floss dispensing device 10 constructed in accordance with a preferred embodiment of the present invention.

Dispensing device 10 generally comprises a frame 12 having an interior chamber 14 which is defined by a bottom wall 16 having a side wall 18 extending upwardly from the peripheral edge thereof. Attached to and extending perpendicularly upward from the bottom wall 16 of the frame 12 are a first hollow axle 20 and a second hollow axle 22. Additionally, extending perpendicularly upward from the bottom wall 16 is a separating wall 24, the opposed ends of which are attached to the side wall 18 in a manner wherein the separating wall 24 extends between the first axle 20 and second axle 22.

Extending forwardly from the portion of the side wall 18 disposed furthest from the second axle 22 is a first elongate prong 26 and a second elongate prong 28. In the preferred embodiment, first prong 26 is hollow and communicates with the interior chamber 14 via a first opening 30 formed adjacent the base portion thereof. Similarly, second prong 28 also has a hollow configuration and communicates with the interior chamber 14 via a second opening 32 formed adjacent the base portion thereof. Formed on the distal end of the first prong 26 is a first curved tip 34, while formed on the distal end of the second prong 28 is a second curved tip 36. The first curved tip 34 is formed adjacent a first floss outlet 38, while the second curved tip 36 is formed adjacent a second floss outlet 40. In the preferred embodiment, the first curved tip 34 and second curved tip 36 each point rearwardly toward the side wall 18 and are used to maintain a length of dental floss 72 between the prongs 26 and 28 and to prevent the slippage of the dental floss 72 therefrom, as will be explained below.

Figure 2:
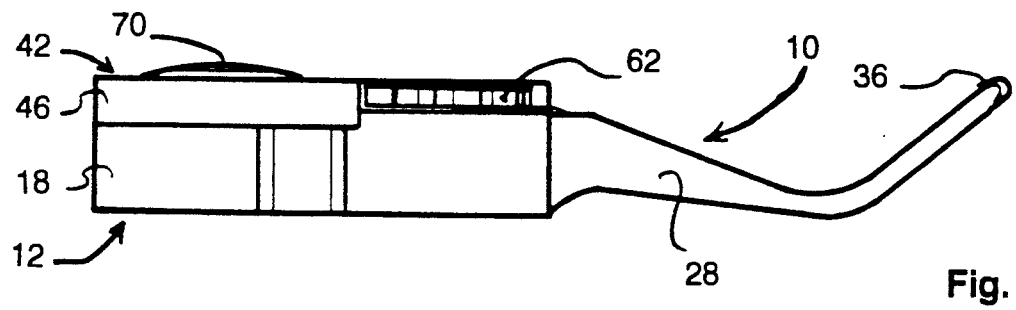
FIG. 2 is a front elevation of the invention.
Figure 3:
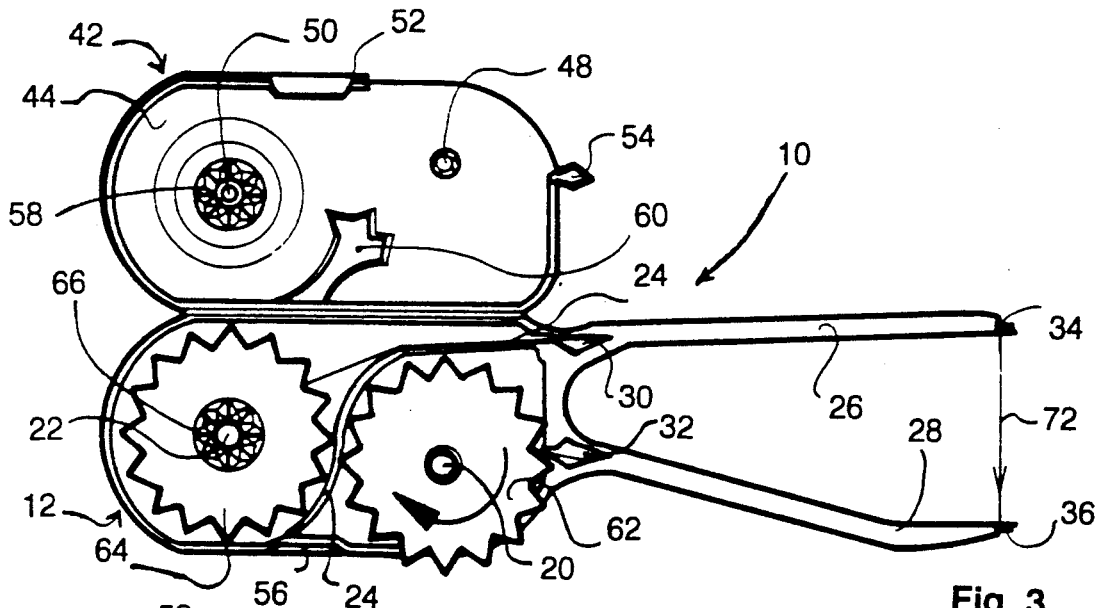
FIG. 3 is a top view of the invention when the lid is open.
Figure 4:
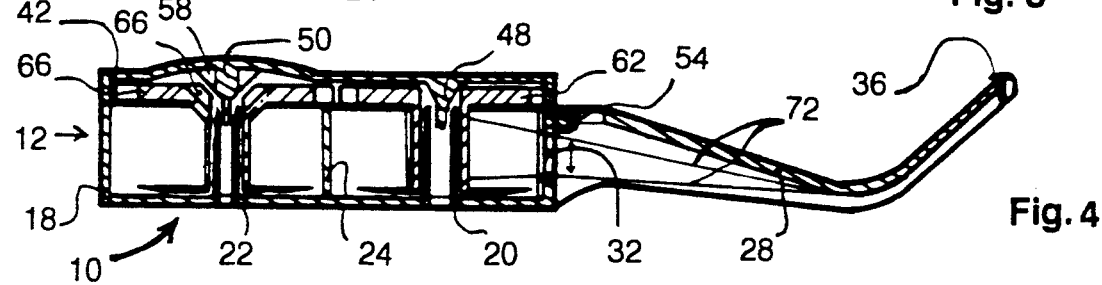
FIG. 4 is a sectional view of the invention, taken along line 4—4 of FIG. 1.
Figure 6:
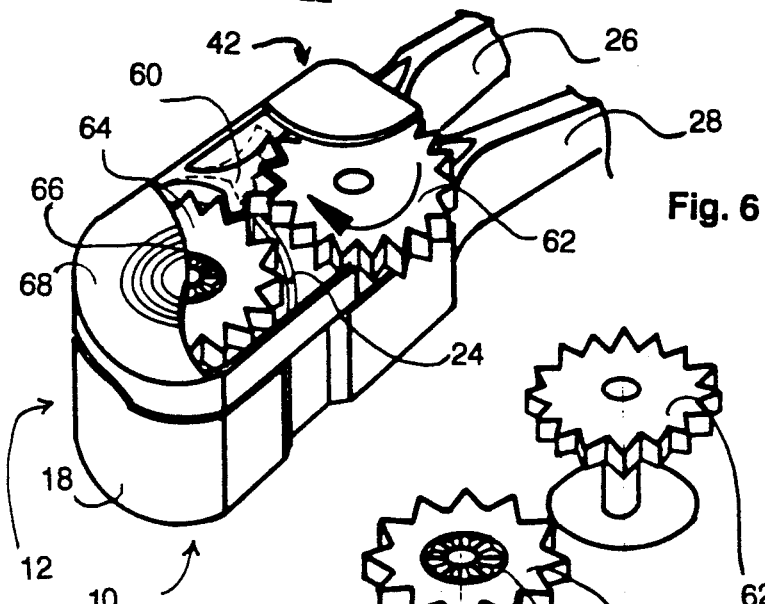
FIG. 6 is a perspective view of the invention, showing the relation of locking mechanism to the spools.
Figure 7:
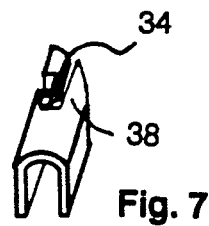
FIG. 7 is an enlarged perspective, detailed view of the tip of the prongs; showing the curve at the tip of the prongs, pointing the opposite direction in order to stop accidental slippage of the floss.
Figure 8:
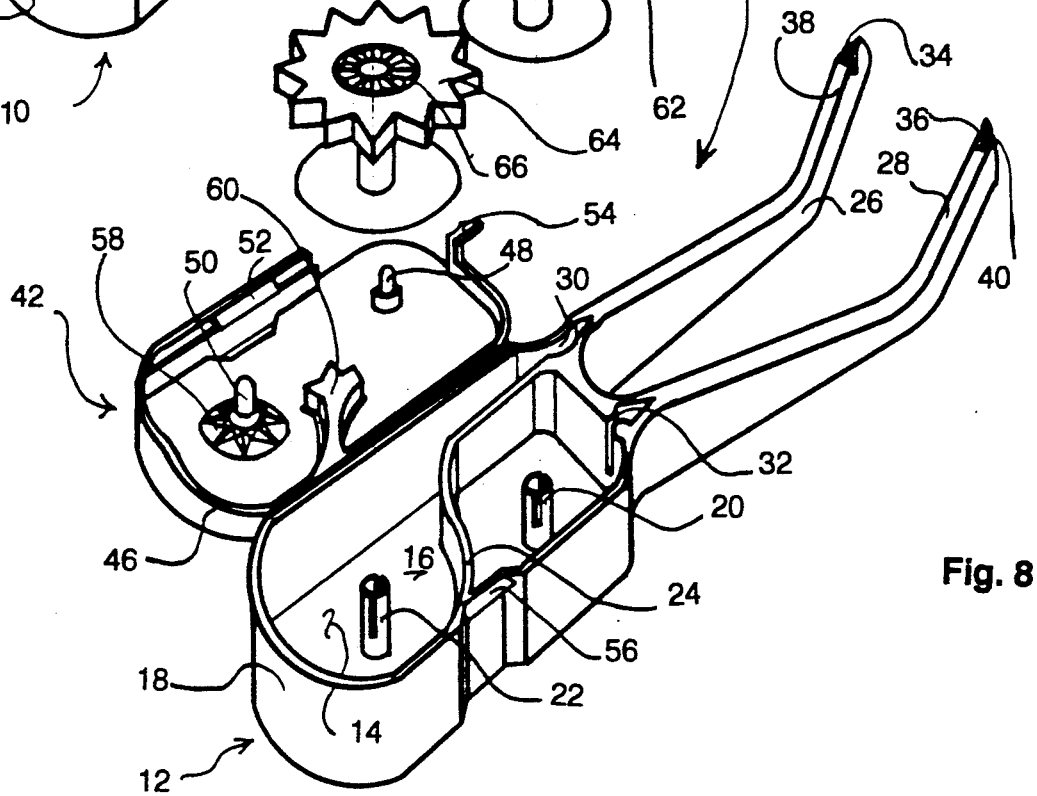
FIG. 8 is an exploded perspective showing the simplicity of the invention and all three parts.

The frame 12 of the dispensing device 10 further includes a lid 42 which is pivotally connected to the side wall 18 of the interior chamber 14 and selectively movable between an open position (as shown in FIGS. 3 and 8) and a closed position (as shown in FIGS. 1, 2 and 6). In the preferred embodiment, lid 42 includes a generally planar portion defining an inner surface 44 having a flange 46 formed partially about and extending upwardly from the peripheral edge thereof. Attached to and extending perpendicularly upward from the inner surface 44 is a first cylinder 48 and a second cylinder 50. First cylinder 48 is sized, configured, and oriented upon the inner surface 44 of the lid 42 so as to be receivable into the open end of the first hollow axle 20 when the lid 42 is in the closed position. Similarly, second cylinder 50 is sized, configured, and oriented upon the inner surface 44 so as to be received into the open end of the second hollow axle 22 when the lid 42 is in the closed position.

Formed along a portion of the upper edge of the flange 46 is a first locking member 52, while extending outwardly from one end of the flange 46 is a second locking member 54. When the lid 42 is moved to the closed position, first locking member 52 is adapted to engage a corresponding locking member 56 formed along a portion of the upper edge of the side wall 18, while second locking member 54 is adapted to be received into and maintained within a portion of the second opening 32. As will be recognized, the engagement of the first locking member 52 to the locking member 56 and the receipt of the second locking member 54 into the second opening 32 maintains the lid 42 in the closed position. Formed on the inner surface 44 of the lid 42 about the base portion of the second cylinder 50 is a first gear 58. Additionally, attached to the flange 46 and extending inwardly along the inner surface 44 of the lid 42 is an elongate, flexible locking member 60. The use of both the first gear 58 and locking member 60 will be explained below.

Figure 5:
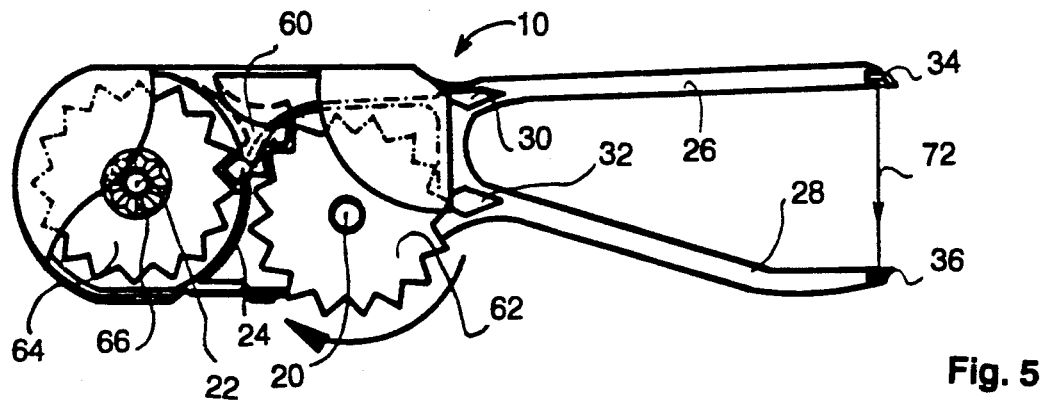
FIG. 5 is a plan view of the invention showing internal parts and the locking mechanism, as if the lid were closed.

Rotatably engaged to the first axle 20 is a first spool 62, while rotatably engaged to the second axle 22 is a second spool 64. As seen in FIG. 3, when the first and second spools 62, 64 are engaged to a respective one of the axles 20, 22, the spools 62, 64 are separated by the separating wall 24 extending within the interior chamber 14. In the preferred embodiment, the first and second spools 62, 64 include circular upper portions having toothed peripheral edges, and are sized such that the upper portions are oriented above the top edges of the side wall 18 and separating wall 24, which are of substantially equal height. As such, when the lid 42 is moved to the closed position, the upper portion of the second spool 64 and most of the upper portion of the first spool 62 are received into the lid 42. Additionally, as seen in FIGS. 3, 5 and 6, the first axle 20 and hence the first spool 62 are oriented within the interior chamber 14 such that a portion of the toothed peripheral edge of the upper portion of the first spool 62 extends outwardly from the frame 12. Since the flange 46 of the lid 42 extends only partially about the inner surface 44 thereof, when the lid 42 is moved to the closed position, a portion of the toothed peripheral edge of the first spool 62 is able to extend outwardly from the frame 12 via the opening formed by the absence of the flange 46.

Formed on the top surface of the upper portion of the second spool 64 is a second gear 66 which has a configuration complimentary to the first gear 58. When the lid 42 is in the closed position and the second cylinder 50 received into the second axle 22, the first gear 58 is oriented in axial alignment with the second gear 66. In the preferred embodiment, the planar portion of the lid 42 possesses sufficient resiliency so as to be deformable in a manner wherein the first gear 58 is engaged to the second gear 66. In this respect, formed on the outer surface 68 of the planar portion of the lid member 42 adjacent the first gear 58 is a raised portion 70 which may be pressed downwardly by the hands or fingers of the user to cause the engagement of the first gear 58 to the second gear 66. Due to the resilient, deformable construction of the planar portion of the lid 42, the downward application of force to the raised portion 70 when the lid 42 is in the closed position causes the concurrent downward movement of the first gear 58, thus causing the same to move into engagement with the second gear 66 of the second spool 64. Importantly, the engagement of the first gear 58 to the second gear 66 prevents the rotation of the second spool 64 for reasons which will be discussed below.

Referring now to FIGS. 5 and 6, when the lid 42 is closed, the locking member 60 allows the first spool 62 and second spool 64 to rotate in only clockwise directions. In this respect, when the lid 42 is closed, the extensions 74 formed on the distal end of the locking member 60 engage the toothed upper portions of the first and second spools 62, 64 in a manner wherein the spools 62, 64 may rotate only in a clockwise direction. As will hereinafter be discussed, the locking member 60 also controls the tension of the dental floss 72 extending between the prongs 34, 36 by allowing the second spool 64 to rotate only in conjunction with the first spool 62. As best seen in FIGS. 5 and 6, when the first spool 62 is rotated in a clockwise direction, the teeth formed about the peripheral edge of the upper portion thereof cause the locking member 60 to pivot away from the upper portion of the second spool 64 toward the flange 46, thus removing the extensions 74 from between the teeth of the second spool 64 in a manner allowing the second spool 64 to be rotated in a clockwise direction. Advantageously, the clockwise rotation of the second spool 64 also serves to push the extensions 74 away from the upper portion of the second spool 64 toward the flange 46, thus allowing the first spool 62 and second spool 64 to rotate simultaneously with each other. When the clockwise rotation of the first spool 62 is stopped, the locking member 60 springs back to its original position away from the flange 46 toward the upper portion of the second spool 64 such that at least one of the extensions 74 is reinserted between the teeth of the second spool 64, thus preventing rotation thereof.

Having thus described the components of the dispensing device 10 of the present invention, the operation thereof will now be described. Initially, the lid 42 is moved to the open position and the second spool 64 removed from upon the second axle 22. A length of clean dental floss 72 is then wound about the cylindrical central portion of the second spool 64 with the second spool 64 being subsequently reengaged to the second axle 22. Thereafter, the dental floss 72 is extended from the second spool 64 and into the hollow interior of the first prong 26 via the first opening 30. The end of the dental floss 72 is then inserted through the first floss outlet 38 and snapped under the first curved tip 34. The dental floss 72 is then extended to the second prong 28 and snapped under the second curved tip 36 prior to being inserted into the second floss outlet 40. After being inserted into the second floss outlet 40, the dental floss 72 is extended through the hollow interior of the second prong 28 and received into the interior chamber 14 via the second opening 32. The end of the dental floss 72 is then wound about the cylindrical central portion of the first spool 62. Thereafter, the lid 42 is moved to the closed position and maintained in such closed position by the engagement of the first locking member 52 to the second locking member 54, and the receipt of the locking member 56 into the second opening 32.

The first and second curved tips 34, 36 are adapted to maintain the dental floss 72 between the first and second prongs 26, 28 and are further adapted to avoid the accidental slippage of the dental floss 72 from between the prongs 26, 28. Additionally, when the lid 42 is closed, the first and second cylinders 48, 50 are received into the first and second axles 20, 22, respectively, and function to stabilize the first and second spools 62, 64 within the frame 12 as well as distribute stress away from the first and second axles 20, 22 to the entire frame 12. The first and second axles 20, 22 are adapted to allow the first and second spools 62, 64 to be freely rotatable in a clockwise direction thereabout when the lid 42 is closed.

During the use of the dispensing device 10, tension is maintained on the dental floss 72 extending between the first prong 26 and second prong 28 by the locking member 60 which prevents the rotation of the second spool 64 independent of the rotation of the first spool 62. When new dental floss is to be disposed between the prongs 26, 28, the first spool 62 is rotated in a clockwise direction by applying a rotational force to the exposed portion of the toothed peripheral edge of the upper portion thereof. As previously explained, rotation of the first spool 62 in the clockwise direction facilitates the simultaneous clockwise rotation of the second spool 64, thus causing the dental floss 72 to unwind from the cylindrical central portion second spool 64 while being simultaneously wound onto the cylindrical central portion of the first spool 62. As seen in FIG. 8, the configuration of the second opening 32 allows the used dental floss 72 to move upwardly or downwardly within the second opening 32 to allow proper winding about the cylindrical central portion of the first spool 62. Additionally, the advancement of the dental floss 72 through the hollow interiors of the first and second prongs 26, 28 maintains the sanitation of the dental floss 72. Because the locking member 60 springs back to its original position when rotation of the first spool 62 is stopped, the tension is maintained on the dental floss extending between the first and second prongs 26, 28 at all times.

In the event greater tension is desired for the dental floss 72 extending between the first and second prongs 26, 28, such tension may be selectively increased by applying downward pressure to the raised portion 70 thereby causing the first gear 58 to engage the second gear 66 to prevent the clockwise rotation of the second spool 64. While the first gear 58 is engaged to the second gear 66, the first spool 62 is then rotated in the clockwise direction, thus increasing the tension on the dental floss 72. Importantly, due to the configuration of the locking member 60, by increasing or decreasing the number of teeth disposed about the peripheral edges of the upper portions first and second spools 62, 64, variations in the constant optimum tension of the dental floss 72 can be obtained.

When the lid 42 is in the closed position, the locking member 60 is supported by the separating wall 24 and, during rotation of the first and second spool 62, 64, slides back and forth over the top edge of the separating wall 24. Additionally, the locking member 60 cannot be disengaged from the second spool 64 by pulling the dental floss 72 at the distal ends of the first and second prongs 26, 28. In this regard, if the dental floss 72 is pulled at the distal ends of the first and second prongs 26, 28, the locking member 60 will be caused to freeze in position. As will be recognized, when the lid 42 is in the open position, free rotation and removal of the first and second spools 62, 64 is allowed, while the movement of the lid 42 to the closed position causes the locking member 60 to engage the first and second spools 62, 64 in the aforementioned manner, thus allowing the dental floss 72 to advance in only one direction. After the dental floss on the second spool 64 has been exhausted, the second spool 64 may be engaged to the first axle 20, with a new spool of dental floss being engaged to the second axle 22.

Additional modifications and improvements of the present invention may also be apparent to those skilled in the art. Thus, the particular combination of parts described and illustrated herein is intended to represent only one embodiment of the invention, and is not intended to serve as limitations of alternative devices within the spirit and scope of the invention.

I claim:

1. A hand-held, portable dental floss dispensing device, comprising:
   a frame comprising:
      a bottom wall defining a peripheral edge;
      a side wall extending about and upwardly from the peripheral edge of said bottom wall, said bottom wall and said side wall defining an interior chamber;
      a pair of prongs extending forwardly from said side wall in spaced relation; and
      a lid pivotally connected to said side wall and selectively movable between open and closed positions, said lid defining inner and outer planar surfaces and including a first gear formed on said inner surface;
   a first spool rotatably mounted within said interior chamber; and
   a second spool rotatably mounted within said interior chamber and defining a top surface including a second gear formed therein having a configuration complimentary to said first gear, said second spool being mounted within said interior chamber in an orientation wherein said second gear is in axial alignment with and spaced from said first gear when said lid is in the closed position;
   said lid being selectively deformable in a manner wherein the application of a downward force to a selected area of the outer surface thereof, when in the closed position, is operable to cause said first gear to engage said second gear so as to prevent rotation of said second spool concurrently with said first spool when a length of dental floss is extended between said first and second spools and said first spool is rotated.

2. The device of claim 1 further comprising a raised portion formed on the outer surface of said lid for facilitating the application of the downward force to the selected area of the outer surface.

3. The device of claim 2 wherein said lid is fabricated from plastic.

4. A hand-held, portable dental floss dispensing device, comprising:
   a frame comprising:
      a bottom wall defining a peripheral edge;
      a side wall extending about and upwardly from the peripheral edge of said bottom wall, said bottom wall and said side wall defining an interior chamber;
      a pair of prongs extending forwardly from said side wall in spaced relation; and
   a lid pivotally connected to said side wall and selectively movable between open and closed positions, said lid defining inner surface having a peripheral edge and a flange extending partially about and downwardly from said peripheral edge;
   a first spool rotatably mounted within said interior chamber;
   a second spool rotatably mounted within said interior chamber; and
   a flexible, elongated lock member attached to and extending inwardly from said flange along said inner surface, said lock member being disposed between and cooperatively engaged to said first and second spools when said lid is in the closed position, and adapted to allow only the clockwise rotation of said first and second spools when disposed therebetween.

5. The device of claim 4 wherein said lock member is further adapted to maintain tension upon a length of dental floss extending from said second spool, between said pair of prongs, and to said first spool when said first spool is not being rotated in a clockwise direction.

6. The device of claim 5 wherein:
said first spool includes a first circular upper portion including a first set of teeth formed about the periphery thereof;
said second spool includes a second circular upper portion including a second set of teeth formed about the periphery thereof; and
said lock member includes at least two extensions formed on the distal end thereof which are cooperatively engaged to said first and second sets of teeth.

7. The device of claim 6 wherein said frame further comprises a separating wall attached to said side wall and extending between said first and second spools, said lock member being supported by and sliding along the top edge of said separating wall when said lid is in the closed position.

8. The device of claim 7 wherein said frame is fabricated from plastic.

* * * * *